United States Patent
Biedermann et al.

(10) Patent No.: US 9,439,778 B2
(45) Date of Patent: Sep. 13, 2016

(54) DEVICE FOR INSERTING AN INTERVERTEBRAL IMPLANT INTO A BODY AND SYSTEM INCLUDING AN INTERVERTEBRAL IMPLANT AND A DEVICE FOR INSERTING SAME

(75) Inventors: Lutz Biedermann, VS-Villingen (DE); Wilfried Matthis, Weisweil (DE)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 0 days.

(21) Appl. No.: 13/523,023

(22) Filed: Jun. 14, 2012

(65) Prior Publication Data

US 2013/0006362 A1   Jan. 3, 2013

Related U.S. Application Data

(60) Provisional application No. 61/496,804, filed on Jun. 14, 2011.

(30) Foreign Application Priority Data

Jun. 14, 2011  (EP) ..................... 11169886

(51) Int. Cl.
*A61F 2/44* (2006.01)
*A61B 17/70* (2006.01)
(Continued)

(52) U.S. Cl.
CPC ............ *A61F 2/4465* (2013.01); *A61F 2/4611* (2013.01); *A61F 2002/2835* (2013.01);
(Continued)

(58) Field of Classification Search
CPC  A61B 17/7074; A61B 17/808; A61B 17/88; A61F 2/4465; A61F 2/4611; A61F 2/46; A61F 2/4603

USPC .......... 623/17.11–17.16; 606/99, 104, 86 A, 606/86 B

See application file for complete search history.

(56) References Cited

U.S. PATENT DOCUMENTS 5,683,399 A * 11/1997 Jones .............................. 606/91
6,500,132 B1 * 12/2002 Li ................................ 600/594
(Continued)

FOREIGN PATENT DOCUMENTS

| DE | 10035182 A1 | 2/2002 |
| DE | 202008011611 U1 | 12/2008 |
| WO | WO 2011/056845 A1 | 5/2011 |

OTHER PUBLICATIONS

Extended European Search Report for European Application No. 11169886.6, extended European Search Report dated Nov. 23, 2011 and mailed Dec. 2, 2011 (7 pgs.).

*Primary Examiner* — Jacqueline Johanas
(74) *Attorney, Agent, or Firm* — Lewis Roca Rothgerber Christie LLP

(57) ABSTRACT

A device for inserting an intervertebral implant into a body includes a flexible end portion having a free end, a thickened portion including an outward protrusion on the flexible end portion at or adjacent the free end, and a stop including an outward protrusion on the flexible end portion positioned at a distance from the free end and spaced apart from the thickened portion, wherein a portion of the flexible end portion between the thickened portion and the stop has outer walls separated by a distance that is less than distances separating outer walls of the thickened end portion and the stop, respectively, and wherein the flexible end portion can assume a first state wherein the outer walls of the portion of the flexible end portion between the thickened portion and the stop are separated by a first distance.

18 Claims, 5 Drawing Sheets

(51) Int. Cl.
*A61F 2/46* (2006.01)
*A61F 2/28* (2006.01)
*A61F 2/30* (2006.01)

(52) U.S. Cl.
CPC ............... *A61F2002/30538* (2013.01); *A61F 2002/30594* (2013.01); *A61F 2002/30596* (2013.01); *A61F 2002/30777* (2013.01); *A61F 2002/30784* (2013.01); *A61F 2002/30789* (2013.01); *A61F 2002/30841* (2013.01); *A61F 2002/30843* (2013.01); *A61F 2002/448* (2013.01); *A61F 2002/4475* (2013.01); *A61F 2002/4623* (2013.01); *A61F 2002/4624* (2013.01); *A61F 2250/0006* (2013.01); *A61F 2310/00023* (2013.01); *Y10T 29/49826* (2015.01)

(56) References Cited

U.S. PATENT DOCUMENTS

| | | | |
|---|---|---|---|
| 7,235,082 B2* | 6/2007 | Bartish et al. | 606/99 |
| 7,479,160 B2* | 1/2009 | Branch et al. | 623/17.11 |
| 7,901,458 B2* | 3/2011 | DeRidder et al. | 623/17.11 |
| 7,935,148 B2* | 5/2011 | Edie et al. | 623/17.16 |
| 7,947,047 B2* | 5/2011 | Arnal | 606/104 |
| 7,976,549 B2* | 7/2011 | Dye et al. | 606/99 |
| 8,439,593 B2* | 5/2013 | Slater et al. | 403/361 |
| 8,579,911 B2* | 11/2013 | Dudasik | 606/99 |
| 2003/0149438 A1 | 8/2003 | Nichols et al. | |
| 2004/0153065 A1* | 8/2004 | Lim | A61F 2/442 606/53 |
| 2005/0038431 A1 | 2/2005 | Bartish et al. | |
| 2005/0080422 A1 | 4/2005 | Otte et al. | |
| 2005/0096745 A1* | 5/2005 | Andre et al. | 623/17.11 |
| 2005/0228400 A1* | 10/2005 | Chao et al. | 606/104 |
| 2006/0095043 A1* | 5/2006 | Martz et al. | 606/90 |
| 2006/0229627 A1 | 10/2006 | Hunt et al. | |
| 2007/0162129 A1 | 7/2007 | Edie et al. | |
| 2007/0213737 A1* | 9/2007 | Schermerhorn et al. | 606/86 |
| 2007/0213826 A1 | 9/2007 | Smith et al. | |
| 2008/0091211 A1 | 4/2008 | Gately | |
| 2008/0119935 A1* | 5/2008 | Alvarez | 623/17.16 |
| 2008/0221694 A1 | 9/2008 | Warnick et al. | |
| 2008/0269768 A1* | 10/2008 | Schwager et al. | 606/104 |
| 2009/0048604 A1 | 2/2009 | Milz et al. | |
| 2010/0094422 A1 | 4/2010 | Hansell et al. | |
| 2010/0114105 A1 | 5/2010 | Butters et al. | |
| 2010/0179660 A1 | 7/2010 | Peukert et al. | |
| 2010/0204798 A1 | 8/2010 | Gerbec et al. | |
| 2010/0256759 A1 | 10/2010 | Hansell et al. | |
| 2011/0172776 A1* | 7/2011 | Warnick et al. | 623/17.16 |
| 2011/0306984 A1* | 12/2011 | Sasing | 606/104 |
| 2012/0277877 A1* | 11/2012 | Smith et al. | 623/17.16 |

* cited by examiner

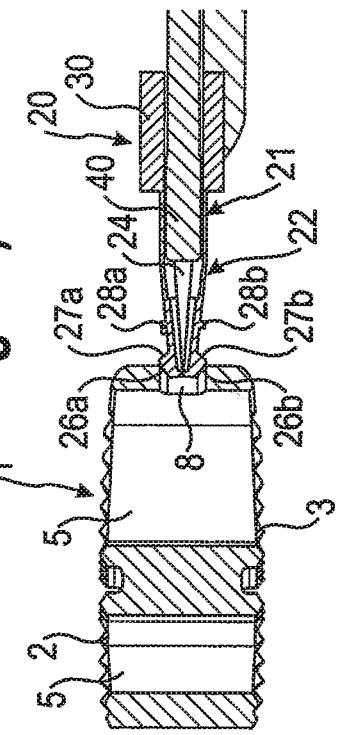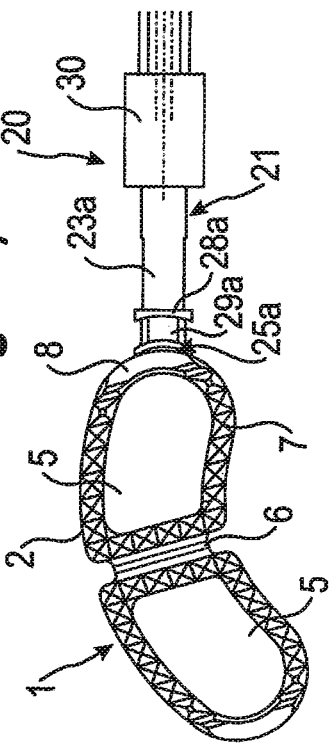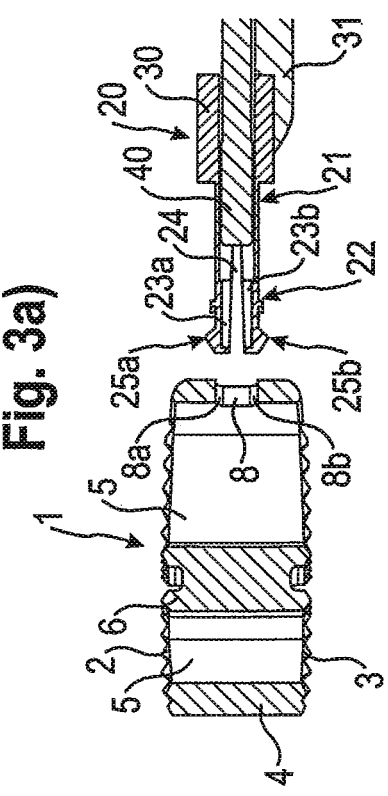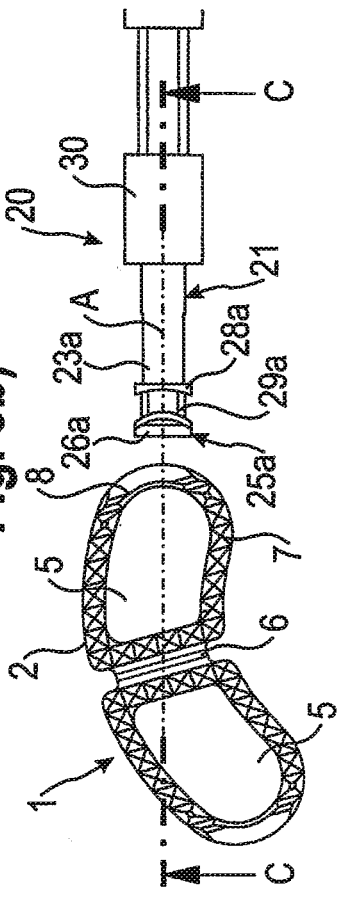

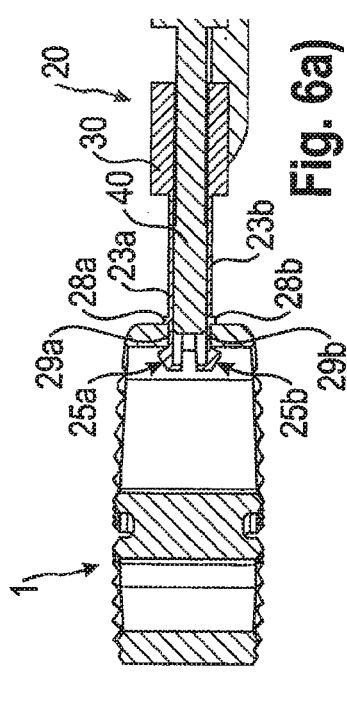 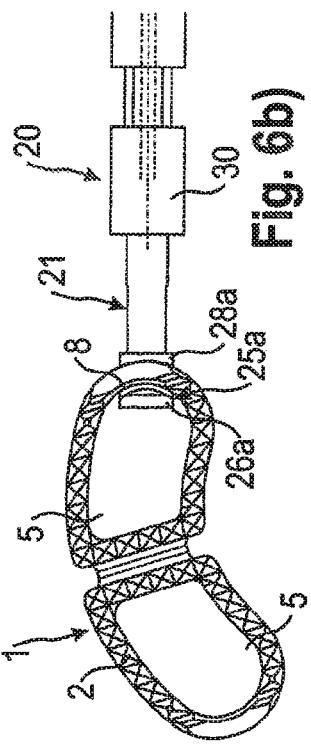 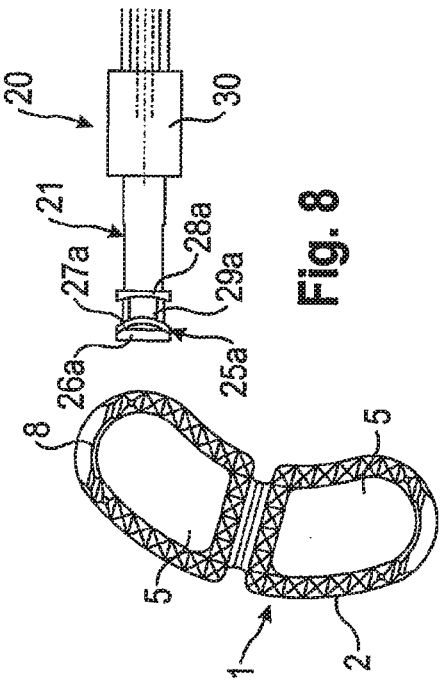
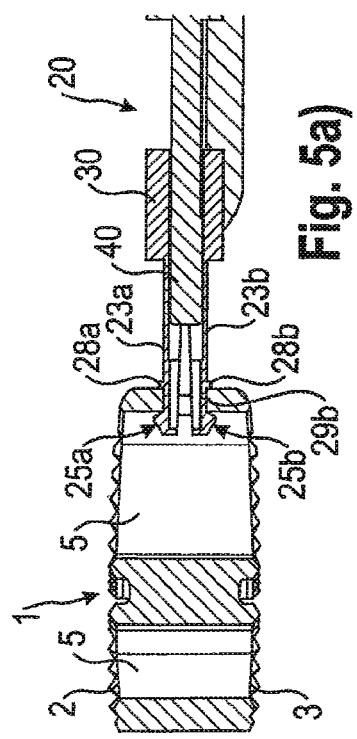 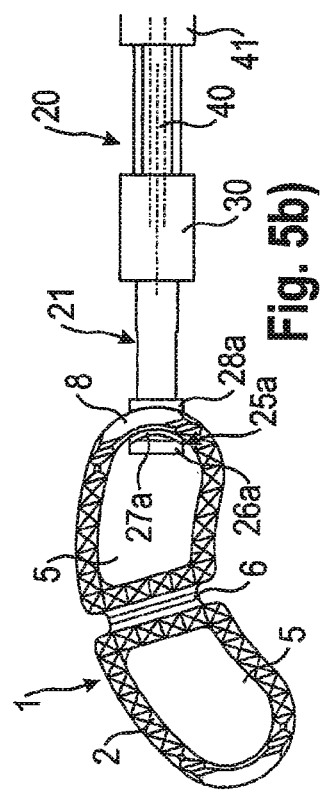 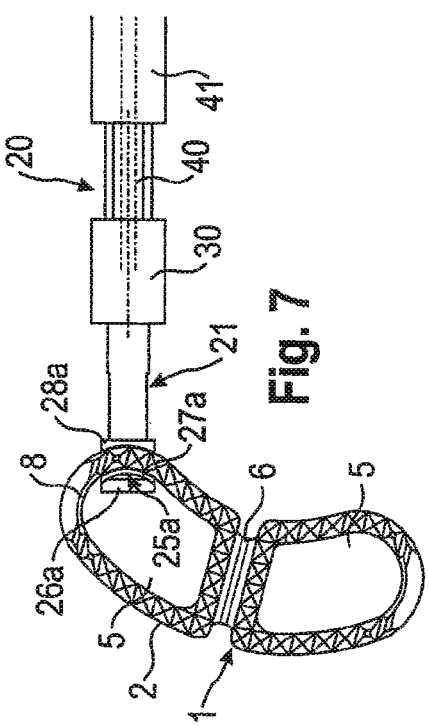

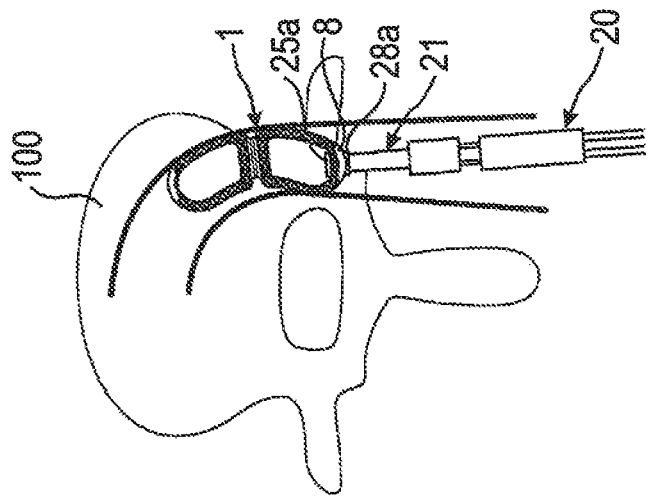
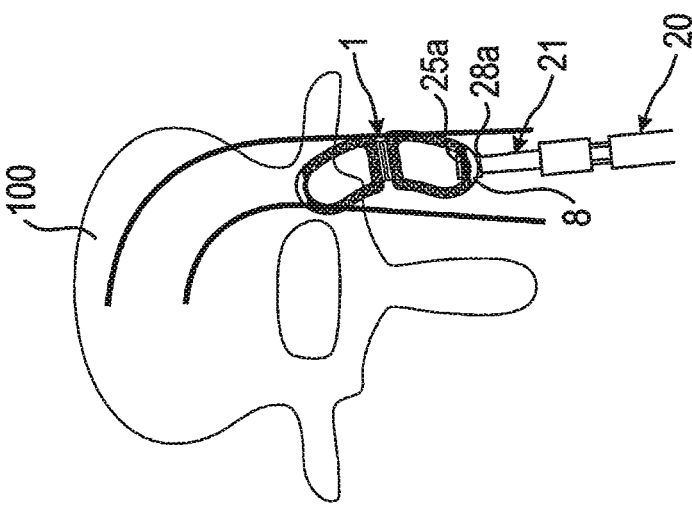
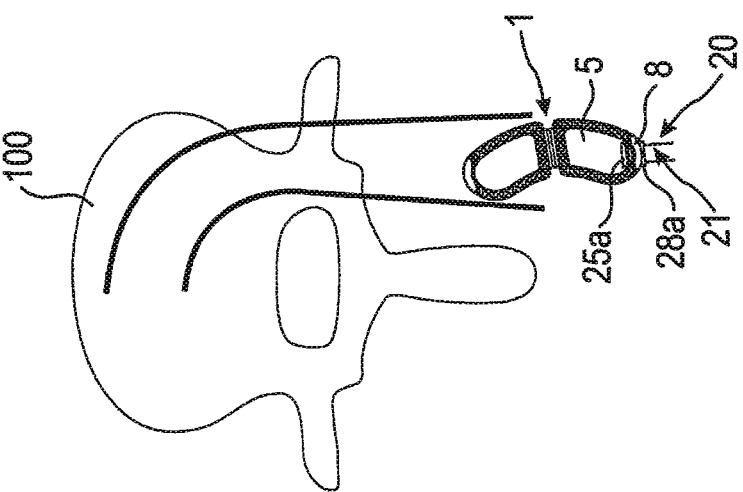

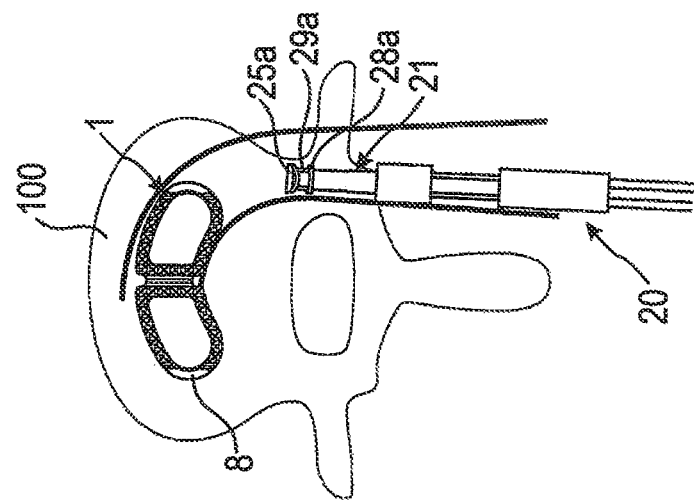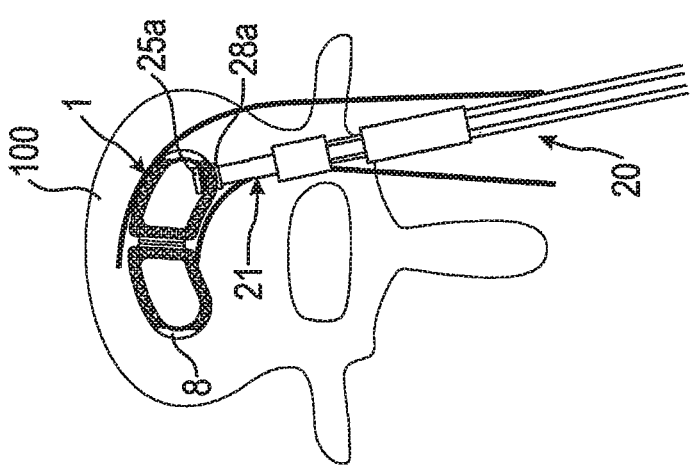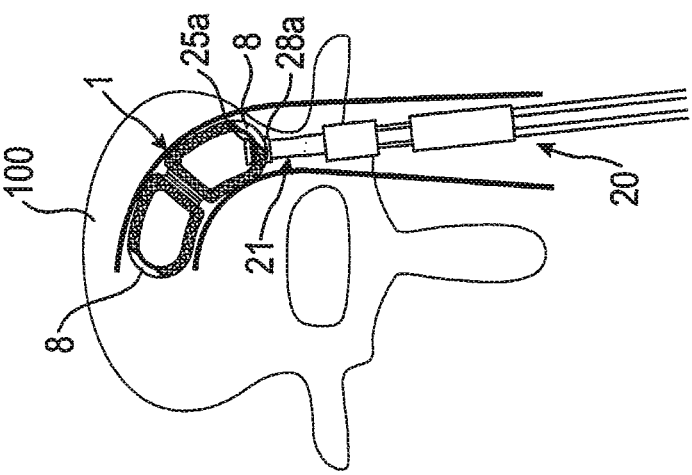

DEVICE FOR INSERTING AN INTERVERTEBRAL IMPLANT INTO A BODY AND SYSTEM INCLUDING AN INTERVERTEBRAL IMPLANT AND A DEVICE FOR INSERTING SAME

CROSS-REFERENCE TO RELATED APPLICATION(S)

The present application claims the benefit of U.S. Provisional Patent Application Ser. No. 61/496,804, filed Jun. 14, 2011, the contents of which are hereby incorporated by reference in their entirety, and claims priority to European Patent Application EP 11 169 886.6, filed Jun. 14, 2011 the contents of which are hereby incorporated by reference in their entirety.

BACKGROUND

1. Field of the Invention

The invention relates to a device for inserting an intervertebral implant into a body, and to a system including the intervertebral implant and the device. The intervertebral implant has a top surface configured to engage a first vertebral body, a bottom surface configured to engage a second vertebral body, and a side wall connecting the top surface and the bottom surface. In the side wall, an elongate opening is provided. The device for inserting the intervertebral implant includes a flexible end portion that can assume a first state where the end portion can be introduced into and removed through the opening, and a second state where the end portion cannot be removed from the implant. In the second state the device may be connected to the intervertebral implant, where the implant and the device may be movable relative to each other along the elongate opening.

2. Description of Related Art

A device for the insertion of surgical implants is known from U.S. Pat. No. 7,235,082 B2. The device includes a shaft defining a conduit and having proximal and a distal end. At least one movable element is provided that includes a leg extending through the conduit and a foot. The movable element is movable relative to the shaft between a first position, wherein the foot extends beyond the distal end and a second position, wherein the foot is substantially adjacent to the distal end and wherein the distal end extends through an opening of the implant.

An intervertebral implant configured to engage with an insertion device for inserting between first and second vertebral members is known from US 2007/0162129 A1. The intervertebral implant has an opening including an elongated shape that extends through the side wall. A connection member including a receptacle is contained within the side wall. The insertion device has a first end that may be configured to connect with the connection member of the implant body. The first end may be selectively positionable between orientations to provide for the connection.

SUMMARY

It is an object of the invention to provide a device for inserting an intervertebral implant, and a system including such an intervertebral implant and device, that is simplified in terms of its use and that is more flexible or adjustable in terms of the final positioning of the implant.

The device for inserting the intervertebral implant simplifies the procedure of insertion, since the connection between the device and the implant can be easily fixed and loosened. When the connection is loose, the implant can be moved into a desired position by rotating the implant relative to the device in a plane that extends through the center of the side wall. A design of the device for inserting the implant ensures that a maximum or large portion of a hollow interior space of the implant can be used for fusion.

When the intervertebral implant is rotated to achieve a desired position between vertebrae, it is safely held by the device and protected against being disconnected from the device.

Final positioning of the implant and removal of the device is also simplified.

Existing intervertebral implants can also be modified to be adapted to the insertion device.

BRIEF DESCRIPTION OF THE DRAWINGS

Further features and advantages of the invention will become apparent from the description of the accompanying drawings. In the drawings:

FIG. 3a shows a cross-sectional view of the intervertebral implant and an end portion of the device for insertion according to an embodiment, where the cross-section is taken along line C-C of FIG. 3b;

FIG. 3b shows a top view of the system including the intervertebral implant and the portion of the device shown in FIG. 3a;

FIG. 4a shows a cross-sectional view of the intervertebral implant and the device for insertion according to an embodiment, where the device is in a first state that allows for introduction or insertion into an opening of the implant;

FIG. 4b shows a top view of the system shown in FIG. 4a;

FIG. 5a shows a cross-sectional view of the intervertebral implant and the device introduced into the opening of the implant according to an embodiment, where a pin of the device is in a retracted position;

FIG. 5b shows a top view of the intervertebral implant and the device of FIG. 5a;

FIG. 6a shows a cross-sectional view of the intervertebral implant and the device introduced into the opening of the implant according to an embodiment, where the pin of the device is in a protruding or extended position;

FIG. 6b shows the intervertebral implant and the device of FIG. 6a in a top view;

FIG. 7 shows the intervertebral implant and the device inserted into the opening of the intervertebral implant according to an embodiment, where the intervertebral implant is rotated relative to the device in a plane extending through the center of the side wall of the implant;

FIG. 8 shows the intervertebral implant and the device removed from the intervertebral implant according to an embodiment; and FIGS. 9a to 9f show steps for inserting and positioning the intervertebral implant into a body according to an embodiment.

DETAILED DESCRIPTION

Figure 1:
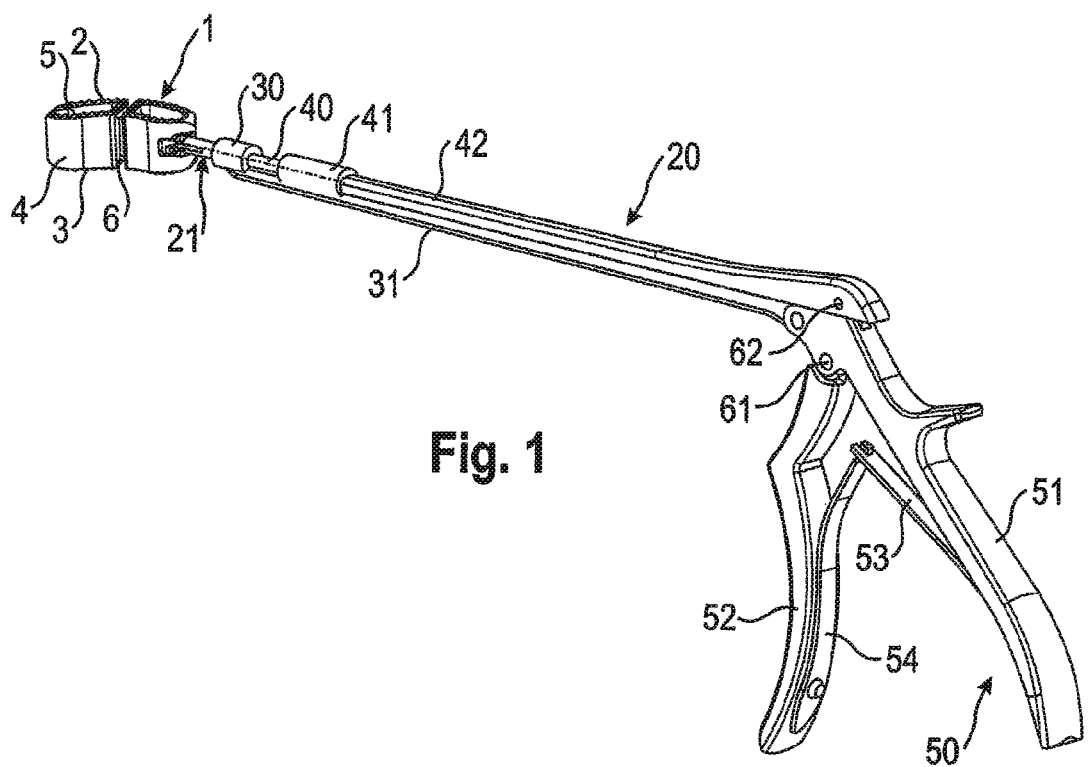
FIG. 1 shows a perspective view of an embodiment of a system including an intervertebral implant and a device for inserting or implanting the intervertebral implant.

FIG. 1 shows a perspective view of one embodiment of an intervertebral implant 1 and a device 20 for inserting the intervertebral implant 1 into, for example, a patient, where the device 20 is attached to the implant 1. As shown in particular in FIGS. 1 and 2, the intervertebral implant 1 includes a top face 2 and a bottom face 3 that are configured to engage respective end plates of a first vertebral body and a neighboring second vertebral body. The top face 2 and the bottom face 3 are connected via a side wall 4 that defines an interior hollow section 5. Generally, the top face 2 and the bottom face 3 have openings so that the hollow interior section 5 extends into the top face 2 and the bottom face 3. In the embodiment shown, the top face 2 and the bottom face 3 are formed by the upper and lower rims of the side wall 4, respectively. Furthermore, a center wall 6 may be provided that separates the hollow interior section 5 in two parts. The height of the side wall 4 is sized so as to allow insertion of the implant 1 between a first and a second vertebral body. The height of the implant 1 may be larger at the center wall 6 and may decrease towards outer ends of the implant 1. Teeth 7 or other engagement portions are provided that project from the top face 2 and the bottom face 3 for engaging the respective end plates.

In the embodiment shown, the implant 1 has two opposing long sides 4a and two opposing short sides 4b connecting the long sides 4a. The short sides 4b may be rounded. The contour of side wall 4 may be arcuate, for example it may have a kidney-shape or a banana-shape.

Figure 2:
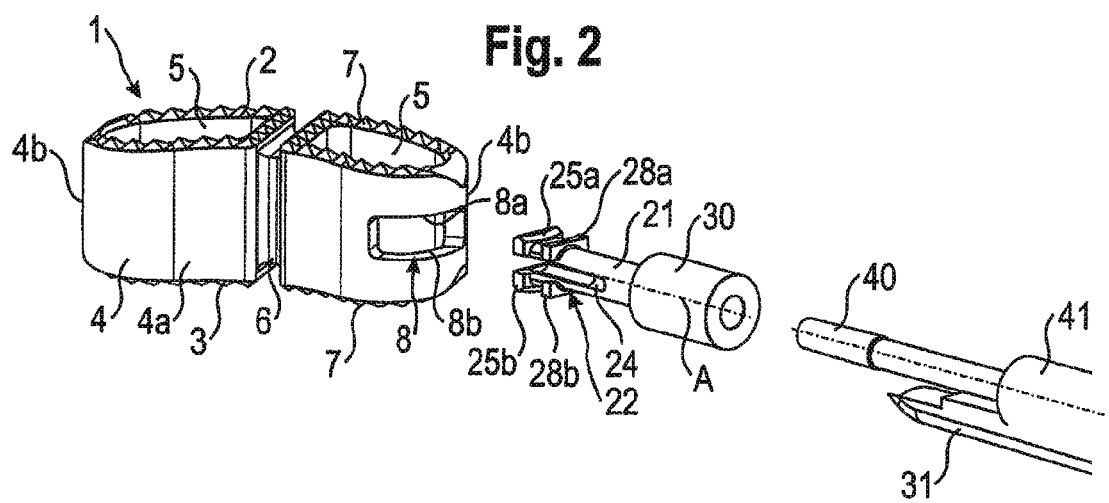
FIG. 2 shows an exploded perspective view of the system of FIG. 1, where a portion of the device for insertion is depicted.

As shown in particular in FIG. 2, an opening 8 in the side wall 4 is provided that extends completely through the side wall 4 into the interior hollow section 5. The opening 8 has an elongate shape and extends preferably over a length in a circumferential direction along a short side 4b. The opening 8 may have a substantially rectangular contour with an upper edge 8a and a lower edge 8b, and may be located substantially in a middle of the side wall 4 along a vertical direction between the top face 2 and the bottom face 3.

The implant 1 shown in the embodiment is only an example. The contour and shape of the implant may be different according to the specific clinical requirements. For example, the contour may have any other shape, such as circular, rectangular, oval, etc. In some embodiments, the height of the side wall may be constant throughout the implant. The opening can be at another position. Only one opening or more than one opening may be provided. Also, it may be possible to adapt existing intervertebral implants without an opening, by providing it with such an opening. Further, in some embodiments, the center wall can be omitted.

An embodiment of the device for inserting the intervertebral implant into, for example, a body of a patient, will now be explained with reference to FIGS. 1 to 8. The device 20 includes an end portion 21 that is configured to be introduced into the opening 8 of the intervertebral implant 1 and to hold the intervertebral implant 1. The end portion 21 is a sleeve-like member having a flexible front portion 22. The flexible front portion 22 is formed by two opposing tongues 23a, 23b that are formed or separated by a slot 24 extending from a free edge of the sleeve-like end portion 21 through opposing portions or sides of the end portion 21.

Each tongue 23a, 23b includes at its free end a thickened portion 25a, 25b. The thickened portions 25a, 25b extend outward so that an outer diameter of the tongues is increased, as can be seen, for example, in FIGS. 3a and 3b. A contour or shape of the thickened portions 25a, 25b seen in a direction perpendicular to the sleeve axis A may be substantially rectangular. The thickened portions 25a, 25b each have a chamfered front wall 26a, 26b and a chamfered rear wall 27a, 27b. The rear walls 27a, 27b may be curved, with a curvature corresponding to a curvature of the side wall 4 in the region of the opening 8.

In addition, each tongue 23a, 23b has an outwardly extending rib 28a, 28b positioned at a distance from the thickened portion 25a, 25b, where said distance is equal or greater than a wall thickness of the side wall 4 of the implant 1 at the opening 8. Hence, portions of the side wall 4 around the opening 8 of the intervertebral implant 1 fit into portions 29a, 29b between portions 25a, 25b and ribs 28a, 28b, respectively. In a top view, as shown in FIGS. 3b and 4b, a side of the ribs 28a, 28b that face the free end of the sleeve-like end portion 21 may be inwardly curved. The curvature may correspond to the curvature of the side wall 4 in the region of the opening 8. The portions 29a, 29b between the thickened portions 25a, 25b and the ribs 28a, 28b may be flat to allow for even contact with the upper and lower edges 8a, 8b of the opening, respectively.

The outer diameter of the flexible front portion 22 of the sleeve-like end portion 21 is sized such that in a non-compressed state of the tongues 23a, 23b (e.g., when the tongues 23a, 23b are not biased towards one another) the thickened portions 25a, 25b form a maximum outer diameter or height that is greater than a height of the opening 8. Also, when the tongues 23a, 23b are not compressed, the outer diameter or height formed by the portions 28a, 28b is also slightly larger than the height of the opening 8. Meanwhile, an outer diameter or height of the end portion 21 formed by the portions 29a, 29b is smaller than the height of the opening 8. The length and width and other sizes and properties of the slot 24 are such that it allows compression of the tongues 23a, 23b towards each other and introduction of the flexible front portion 22 into the opening 8 of the intervertebral implant 1. An outer diameter or width of the sleeve-like end portion 21 at the position of the slot 24 is smaller than the length of the elongate opening 8, so that the flexible front portion 22 may move along the length of the elongate opening 8 in a circumferential or horizontal direction.

The sleeve-like end portion 21 has a rear portion 30 with a larger outer diameter. The rear portion 30 may be connected to a first grip portion 51 of a tongs-like handle 50 that includes the first grip portion 51 and a second grip portion 52.

The device 20 for inserting the implant 1 further includes a pin 40 extending into the sleeve-like end portion 21. The pin 40 has an outer diameter that allows it to slide within the sleeve-like end portion 21. An inner diameter of the flexible front portion 22 of the sleeve-like end portion 21 is slightly smaller than the outer diameter of the pin 40, so that, when the pin 40 is moved between the tongues 23a, 23b, it slightly spreads the tongues 23a, 23b apart from each other. Thus, the sleeve-like end portion 21 and the pin 40 cooperate in the manner similar to a collet chuck with pin. The pin 40 is mounted to a portion 41 with an outer diameter greater than that of the pin 40, and can slide in or relative to a connection bar 31 that connects the sleeve-like end portion 21 with the grip portion 51. The pin 40 is connected through or via a connection bar 42 with the other grip portion 52 of the handle 50. The grip portions 51, 52 are connected via hinges 61, 62 to the connection bars 31, 42, respectively, so that, like with tongs, a moving of the grip portions 51, 52 towards each other moves the pin 40 relative to the sleeve-like end portion 21.

The pin 40 can assume a first position in which it is retracted relative to the tongues 23a, 23b, as shown, for example in FIGS. 3a to 4b. The pin further can assume a second position in which it protrudes into the sleeve-like end portion 21 between the tongues 23a, 23b, and spreads them apart.

The grip portions 51, 52 are biased away from each other via leaf springs 53, 54. Due to the hinges 61, 62, the handle 50 is arranged at an angle with respect to the connecting bars 31, 42. This facilitates handling and increases the possibilities for bringing the implant to its final position.

The connection of the pin 40 and the sleeve-like end portion 21 to the handle 50 is only exemplary. Other constructions and other types of handles can be used to achieve the relative movement of the pin with respect to the sleeve-like end portion as described above.

The implant 1, as well as the portions of the device 20 for inserting the implant 1, that may come in contact with a patient's body, are made of a biocompatible material. For example, the implant 1 and/or the device 20 may be made of stainless steel or titanium, or of a biocompatible metal alloy, such as a nickel-titanium alloy, or may be made of a biocompatible plastic material, such as for example, PEEK (polyetheretherketone).

Operation of the device 20 for inserting the implant 1 will now be explained with reference to FIGS. 3 to 9. The device 20 and the implant 1 are oriented relative to each other such that the slot is parallel to or aligned with the upper and/or lower edge of the elongate opening. Hence, the tongues are on top of each other as seen from a height direction of the implant (See, e.g., FIG. 3a). First, as shown in FIGS. 3a and 3b, the pin 40 is in the first position, which is the retracted position. The tongues 23a, 23b are configured to be flexibly pressed towards each other, as shown in FIG. 4a. When the tongues 23a, 23b are pressed towards each other, the flexible front portion 22 can be introduced into the elongate opening 8 of the implant 1, During introduction, the chamfered front walls 26a, 26b of the tongues 23a, 23b slide along the upper and lower edges 8a, 8b of the elongate opening 8, respectively, until the uppermost and lowermost portions of the thickened portions 25a, 25b are in contact with the upper and lower edge 8a, 8b of the elongate opening 8, respectively. This maintains or keeps the tongues 23a, 23b in a compressed state during the introduction. The tongues 23a, 23b may be slightly pre-compressed by bending them towards each other when the pin 40 is in the retracted position.

When the thickened portions 25a, 25b of the flexible front portion 22 have passed the elongate opening 8 and have entered the hollow interior section 5 of the implant 1, the tongues 23a, 23b spread back apart from each other until the upper and lower edges 8a, 8b of the elongate opening rest in the space portions 29a, 29b, respectively, as can be seen in FIGS. 5a to 6b. In this condition, the tongues 23a, 23b can still initially be compressed towards each other. This makes it possible to move the flexible front portion 22 in the elongate opening 8 along the lengthwise direction of the opening. Hence, the flexible front portion 22 can be moved to a suitable position relative to implant 1 for introducing the implant 1 into the surgical site. The ribs 28a, 28b act as stops that prevent further introduction or insertion of the device 20 into the implant 1.

When the implant 1 and the device 20 for inserting the implant 1 are positioned correctly or in a desired position with respect to each other, the pin 40 is pushed further into the flexible front portion 22, thereby spreading the tongues 23a, 23b slightly apart from each other until they abut against the upper and lower edges 8a, 8b of the elongate opening 8, respectively. Thereby, the implant 1 is firmly held through engagement of the upper and lower edges 8a, 8b of the opening 8 with the portions 29a, 29b of the sleeve-like end portion 21. This is shown in particular in FIGS. 6a and 6b.

After the implant 1 has been positioned at the desired implantation site, the pin 40 is moved back from its second position into the retracted position, and the tongues 23a, 23b may be drawn out and removed from the opening 8. Due to the chamfered rear walls 27a, 27b, the tongues 23a, 23b can be pressed together when the flexible front portion 22 is drawn out from the implant 8. This allows for retracting the flexible front portion 22 back through the elongate opening 8.

The use and implantation of the implant 1 during surgery will now be described with respect to FIGS. 9a to 9f. FIGS. 9a to 9f show steps for inserting and positioning the intervertebral implant 1 into a body. First, as shown in FIG. 9a, the device 20 is connected to the implant 1, preferably in such a way that the flexible front portion 22 is positioned at approximately a center of the elongate opening 8 in a lengthwise direction. By moving the pin 40 into the second position, the connection between the implant 1 and the device 20 can be fixed. Then the implant 1 is introduced into an intervertebral space between two neighboring vertebrae, where one of them is shown as vertebra 100 in the drawings. The narrow side 4b of the implant 1 opposite to where the device 20 is connected may serve as a leading side. In the method shown, the intervertebral implant 1 is introduced in the space between the vertebral bodies 100 using a posterior and lateral approach to access the space between the vertebral bodies 100.

When the implant 1 and the device 20 experience resistance and cannot be pushed further, for example, as shown in FIG. 9c, the fixation between the implant 1 and the device 20 is loosened by, for example, retracting the pin 40 back into the first position. Then, the implant 1 and the device 20 may be movable relative to each other, because the sleeve-like end portion 21 can move in the elongate opening 8. By means of this, an angle between the implant 1 and the device 20 can be changed. As shown in FIGS. 9c to 9e, the implant 100 can then be pushed into its end position between the vertebral bodies 100.

Thereafter, the device 20 is removed or detached from the implant 1 by drawing the flexible front portion 22 out of the opening 8.

Since the device 20 can be connected to and separated from the implant 1 in an easy manner, handling of the respective parts is simplified. In addition, due to the thickened portions and the ribs of the device 20 that act as stops, inadvertent removal of the device 20 during the process of inserting the implant 1 can be prevented.

Various modifications of the device for inserting the implant are also possible. For example, a number of the flexible tongues may vary. Also the shape of the tongues can vary. Further, in some embodiments, instead of the pin, another spreading member or mechanism can be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A device for inserting an intervertebral implant into a body, the intervertebral implant having a top surface configured to engage a first vertebral body, a bottom surface configured to engage a second vertebral body, a sidewall connecting the top surface and the bottom surface, and an elongate opening in the sidewall, the elongate opening having a height and a length greater than the height, the device comprising:
- a flexible end portion having a free end configured for insertion into and removal from the elongate opening of the implant;
- a thickened portion comprising an outward protrusion on the flexible end portion at or adjacent the free end;
- a stop comprising an outward protrusion on the flexible end portion positioned at a distance from the free end, the stop being spaced apart from the thickened portion by a fixed distance and configured to limit insertion of the flexible end portion into the elongate opening of the implant; and
- a spreading element slidably arranged along the flexible end portion, an outermost diameter or width of the spreading element being smaller than a width or diameter of the flexible end portion,
- wherein a portion of the flexible end portion between the thickened portion and the stop comprises a groove.

2. The device of claim 1, wherein the flexible end portion comprises at least two tongues separated by a slot,
- wherein the flexible end portion is configured to assume a first state and a second state,
- wherein, in the first state, the spreading element is a first distance from a free end of the flexible end portion and the flexible end portion has at least a first height, and
- wherein, in the second state, the spreading element is a second distance from the free end of the flexible end portion, the second distance being greater than the first distance, and the flexible end portion has a second height that is less than or equal to the first height.

3. The device of claim 2, wherein the spreading element comprises a pin that is configured to assume a retracted position and a protruding position,
- wherein, in the retracted position, the flexible end portion is configured to be deformable between the first state and the second state, and
- wherein, in the protruding position, the pin protrudes farther into the flexible end portion than in the retracted position to prevent the flexible end portion from assuming the second state.

4. The device of claim 1, wherein the flexible end portion and the spreading element are each connected to a grip portion of a handle of the device.

5. The device of claim 4, wherein the handle is configured to move the spreading element relative to the flexible end portion.

6. The device of claim 1, wherein the flexible end portion comprises a chamfered surface portion at the free end that is configured to allow sliding of the flexible end portion along an edge of the elongate opening of the implant.

7. The device of claim 1, wherein the flexible end portion comprises a chamfered rear surface portion facing away from the free end configured to allow sliding of the flexible end portion along an edge of the elongate opening of the implant.

8. The device of claim 1, wherein the stop is curved in a direction toward the thickened portion to adapt to a curved portion of the sidewall around the elongate opening of the implant.

9. The device of claim 1, wherein the flexible end portion comprises at least two tongues separated by a slot, and
- wherein the spreading element is slidably arranged along an inner surface of the at least two tongues adjacent the slot.

10. A device for inserting an intervertebral implant into a body, the intervertebral implant having a top surface configured to engage a first vertebral body, a bottom surface configured to engage a second vertebral body, a sidewall connecting the top surface and the bottom surface, and an elongate opening in a convex portion of the sidewall, the elongate opening having a height and a length greater than the height, the device comprising:
- a flexible end portion having a free end configured for insertion into and removal from the elongate opening of the implant and comprising at least two tongues separated by a slot;
- a thickened portion comprising an outward protrusion on the flexible end portion at or adjacent the free end; and
- a stop comprising an outward protrusion on the flexible end portion positioned at a distance from the free end, the stop being spaced apart from the thickened portion by a fixed distance and configured to limit insertion of the flexible end portion into the implant;
- wherein the stop has a curved surface that is concavely curved in a direction towards the thickened portion corresponding to the convex portion of the sidewall;
- wherein a portion of the flexible end portion between the thickened portion and the stop comprises a groove, one end of the groove being formed by the stop; and
- wherein the thickened portion, the stop, and the groove are on each of the at least two tongues.

11. A system comprising an intervertebral implant and a device for inserting the intervertebral implant into a body, the intervertebral implant comprising:
- a top surface configured to engage a first vertebral body;
- a bottom surface configured to engage a second vertebral body; and
- a sidewall connecting the top surface and the bottom surface;
- wherein an elongate opening is arranged in the sidewall and has a height and a length greater than the height; and the device for inserting the intervertebral implant comprising:
- a flexible end portion having a free end with a width smaller than the length of the elongate opening, the flexible end portion being configured for insertion into and removal from the elongate opening;
- a thickened portion comprising an outward protrusion on the flexible end portion at or adjacent the free end; and
- a stop comprising an outward protrusion on the flexible end portion positioned at a distance from the free end, the stop being spaced apart from the thickened portion by a fixed distance and configured to limit insertion of the flexible end portion into the elongate opening;
- wherein a portion of the flexible end portion between the thickened portion and the stop comprises a groove;
- wherein the flexible end portion is configured to engage the implant to connect the device to the implant; and
- wherein the width of the free end is smaller than the length of the elongate opening such that, when the stop contacts the sidewall of the implant, the flexible end portion is configured to pivot relative to the implant to adjust an angular orientation of the implant relative to the device.

12. The system of claim 11, wherein the flexible end portion is configured to assume a first state and a second state, wherein, in the first state, a distance between outer walls of the thickened portion is greater than the height of the elongate opening and the flexible end portion is configured to engage the implant to connect the device to the implant, and wherein, in the second state, the distance between the outer walls of the thickened portion is less than or equal to the height of the elongate opening and the flexible end portion is insertable into and removable from the elongate opening.

13. The system of claim 11, wherein the elongate opening has an arcuate shape along a plane parallel to the top surface, and wherein the flexible end portion comprises a portion with an arcuate shape corresponding to the arcuate shape of the elongate opening.

14. The system of claim 11, wherein a distance between the outward protrusions at the free end and the stop is greater than a wall thickness around the elongate opening to hold the implant between the outward protrusions of the free end and the stop.

15. The system of claim 11, wherein the outward protrusions extend in a direction of the height of the elongate opening when the flexible end portion is attached to the implant.

16. The system of claim 11, wherein the flexible end portion comprises a chamfered surface portion at the free end that is configured to allow sliding of the flexible end portion along an edge of the elongate opening.

17. The system of claim 11, wherein the flexible end portion comprises a chamfered rear surface portion facing away from the free end configured to allow sliding of the flexible end portion along an edge of the elongate opening.

18. The system of claim 11, wherein the intervertebral implant further comprises a hollow interior section defined by the sidewall and open to the top surface and the bottom surface.

* * * * *

UNITED STATES PATENT AND TRADEMARK OFFICE
CERTIFICATE OF CORRECTION

PATENT NO.        : 9,439,778 B2                                Page 1 of 1
APPLICATION NO.   : 13/523023
DATED             : September 13, 2016
INVENTOR(S)       : Biedermann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 77 days.

Signed and Sealed this
Twenty-fifth Day of September, 2018

Andrei Iancu
*Director of the United States Patent and Trademark Office*